US006936062B2

(12) United States Patent
Hallgrimson

(10) Patent No.: US 6,936,062 B2
(45) Date of Patent: Aug. 30, 2005

(54) TUBULAR CHIROPRACTIC THERAPY TABLE

(76) Inventor: Clint B. Hallgrimson, 649 Cadder Avenue, Kelowna, British Columbia (CA), V1Y 5N5

( * ) Notice: Subject to any disclaimer, the term of this patent is extended or adjusted under 35 U.S.C. 154(b) by 242 days.

(21) Appl. No.: 10/325,599

(22) Filed: Dec. 19, 2002

(65) Prior Publication Data

US 2003/0153950 A1 Aug. 14, 2003

(30) Foreign Application Priority Data

Dec. 19, 2001 (CA) ........................................... 2365583

(51) Int. Cl.[7] ................................................ A61F 5/00

(52) U.S. Cl. .......................... 606/240; 606/241; 5/621; 128/845

(58) Field of Search .................... 601/23, 24; 606/237, 606/240, 241, 242, 243, 244, 245; 128/845, 846; 5/600, 620, 621, 622, 623, 624, 632; D24/183; D6/382; 482/142, 130

(56) References Cited

U.S. PATENT DOCUMENTS

| | | | | | |
|---|---|---|---|---|---|
| 2,693,796 | A | * | 11/1954 | Warner | 601/98 |
| 2,721,106 | A | * | 10/1955 | Walter | 108/147 |
| 3,821,852 | A | * | 7/1974 | Binegar | 606/242 |
| 4,157,089 | A | | 6/1979 | Loughrey | |
| 4,333,637 | A | * | 6/1982 | Shelton | 5/600 |
| 4,333,638 | A | * | 6/1982 | Gillotti | 5/622 |
| 4,390,173 | A | * | 6/1983 | Barnes | 5/624 |
| 4,927,139 | A | * | 5/1990 | Taltre | 5/632 |
| 5,050,589 | A | | 9/1991 | Engle | |
| 5,177,823 | A | * | 1/1993 | Riach | 5/622 |
| 5,472,401 | A | | 12/1995 | Rouillard et al. | |
| 5,562,575 | A | | 10/1996 | Gvoich | |
| 5,642,542 | A | * | 7/1997 | Kometani | 606/242 |
| 6,532,609 | B2 | * | 3/2003 | Taylor et al. | 5/622 |

FOREIGN PATENT DOCUMENTS

| | | |
|---|---|---|
| CA | 1163883 | 3/0000 |
| CA | 1069954 | 1/1980 |
| GB | 2152381 A | 11/1984 |

* cited by examiner

*Primary Examiner*—Gregory L. Huson
*Assistant Examiner*—Quang D. Thanh
(74) *Attorney, Agent, or Firm*—Antony C. Edwards

(57) ABSTRACT

A chiropractic table for treatment of a patient when the patient is in a lordotic, relaxed posture lying prone on the table, includes a base and a padded frame mounted to the base. The frame has an upper side shaped to form an elongate upper surface extending in a generally horizontal longitudinal direction. The upper surface is arcuately shaped, when viewed in lateral cross-section orthogonal to the longitudinal direction. The upper surface has downwardly curved sides extending downwardly and oppositely from an uppermost ridge-line surface extending the length of the upper surface. The ridge-line surface has a face-resting concavity formed thereon at a first end of the upper surface. The concavity is adapted to receive in resting relation thereon the face of the patient when lying prone along and astride the ridge-line surface.

17 Claims, 5 Drawing Sheets

TUBULAR CHIROPRACTIC THERAPY TABLE

CROSS REFERENCE TO RELATED APPLICATION

This application claims priority from Canadian Patent Application No. 2,365,583 filed Dec. 19, 2001 entitled Tubular Chiropractic Therapy Table.

FIELD OF THE INVENTION

This relates to the field of chiropractic therapy and exercise tables and in particular to a tubular table upon which a patient lies for chiropractic therapy and which also serves for exercise applications.

BACKGROUND OF THE INVENTION

In the prior art, applicant is aware of treatment benches and tables such as the Ramped Bench of Roullard et al. which is the subject of U.S. Pat. No. 5,472,401 which issued Dec. 5, 1995, which perhaps exemplifies the prior art which is replete with the use of bench or table surfaces where the patient lies on a planar supporting surface. By way of further example, applicant is aware of United Kingdom Patent Application No. 2 152 381 which was published Aug. 7, 1985 for the Physiotherapy Table of Moomaw. By way of yet further example, applicant is aware of U.S. Pat. No. 4,157,089 which issued Jun. 5, 1979 for the Physiotherapy Table of Loughrey, and U.S. Pat. No. 5,050,589 which issued Sep. 24, 1991 for the Isokinetic Knee Table of Engle.

Non planar therapeutic tables are unknown in the prior art of which applicant is aware without resorting to reference to mere exercise equipment such as the Therapeutic Exercise Equipment for the Handicapped which is the subject of Canadian Patent No. 1,290,209 which issued to Bergeron on Oct. 8, 1991. The Bergeron patent discloses a rigid hemispherical shell having a moulded foam exterior for use in providing therapeutic exercise for a handicapped child. Bergeron teaches that the object of his exercise apparatus is to enhance a handicapped child's ability to maintain balance and proper posture, developing in such a child either higher or lower level balance skills or both. The apparatus is taught as being capable of being used by a physical therapist to initiate a number of different postural and equilibrium reactions in the body of the handicapped child.

In applicant's experience if a patient is laid over a hemispherical shape for example if the patient is laid prone over the device of Bergeron or over an inflatable exercise ball such as are presently commercially available, the result is a kyphotic curvature or dorsal convexity of the spine conforming to the shape of the ball, which is good for stretching but not conducive to myofascial therapy. What is not taught in the prior art of which applicant is aware, and which it is one object of the present invention to provide, is a generally cylindrical or tubular table which allows the lordotic curves of a patient's spine to remain as the patient is left in a relaxed lordotic posture when supine, that is lying along in a "hugging" position on the table. Thus it is a further object to provide such a table whereon the patient is stable when lying supine and in a relaxed lordotic posture thereby being conducive for manipulative and myofascial applications. A further aspect of the present invention is to provide a generally cylindrical or tubular table which provides for exercise and stretching applications in addition to chiropractic therapy, and which may thus provide for all such applications, including weight lifting, strength training, long axis traction, myofascial therapy, manipulative therapy, physiotherapy, surgical applications, and prone and supine relaxing.

SUMMARY OF THE INVENTION

In summary, the chiropractic table of the present invention, for treatment of a patient when the patient is in a lordotic, relaxed posture lying prone on the table, includes a base and a padded frame mounted to the base. The frame has an upper side shaped to form an elongate upper surface extending in a generally horizontal longitudinal direction. The upper surface is arcuately shaped, when viewed in lateral cross-section orthogonal to the longitudinal direction. The upper surface has downwardly curved sides extending downwardly and oppositely from an uppermost ridge-line surface extending the length of the upper surface.

The ridge-line surface has a face-resting concavity formed thereon at a first end of the upper surface. The concavity is adapted to receive in resting relation thereon the face of the patient when lying prone along and astride the ridge-line surface.

A pair of patient leg supports are mounted to a second end of the upper surface opposite the first end. The pair of patient leg supports are for supporting the legs of the patient adjacent the curved sides when the patient is lying prone along and astride the ridge-line surface.

In one embodiment the concavity may have an aperture in it. The aperture may be formed in the ridge-line surface and between the downwardly curved sides. The aperture may extend through the upper surface and through a corresponding portion of the padded frame. A pair of pillows may be mounted on either side of the aperture so that each side of the face of the patient rests on one of the pair of pillows when the patient is lying prone along and astride the ridge-line surface. The pair of pillows may be releasably mounted into the concavity and the concavity may be formed so as to be recessed into the upper surface.

In one embodiment, the base may be pair of upright supports, where one upright support of the pair of upright supports is mounted to the frame at each of the first and second ends of the frame. Each the-upright support may be a post telescopically mounted to the frame for selectively vertically adjustable sliding of the post relative to the frame. The padded frame may be tubular so as to define a cavity along and within the frame. The padded frame may be padded with resilient padding extending along the ridge-line surface and down the curved sides. The outer surface of the padded frame may be generally cylindrical. The upright supports may be mounted to the frame so as to extend telescopically into the cavity. The pair of patient leg supports may be a pair of ankle straps.

DETAILED DESCRIPTION OF EMBODIMENTS OF THE INVENTION

Figure 1:
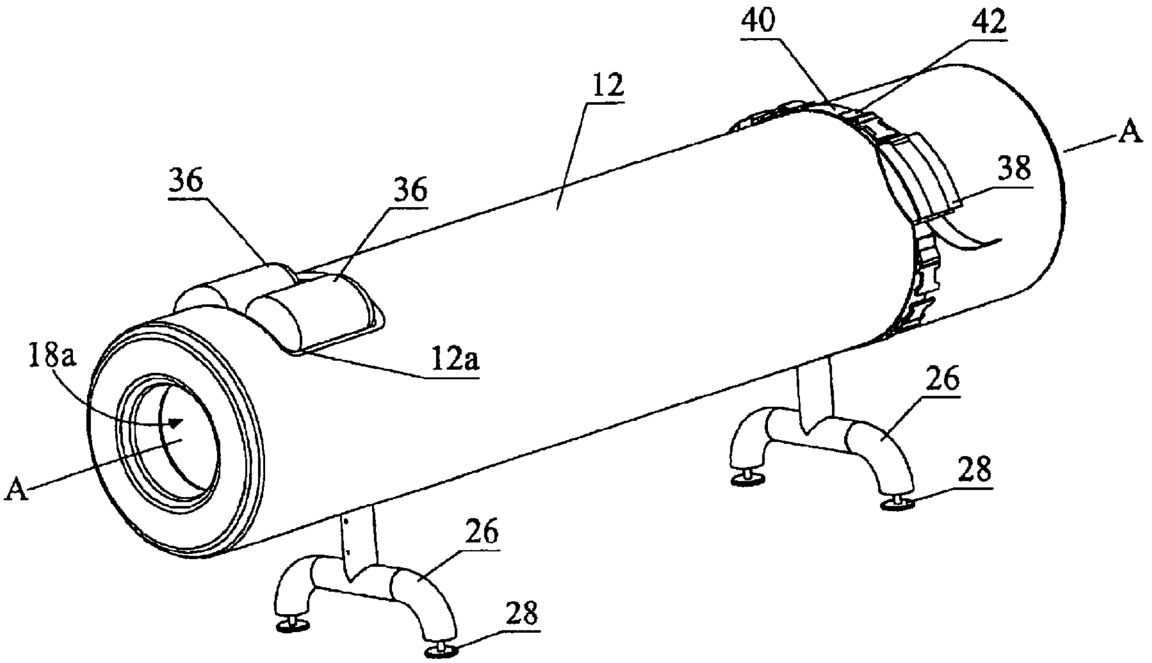
FIG. 1 is, in front perspective view, the chiropractic therapy table according to one embodiment of the present invention.
Figure 2:
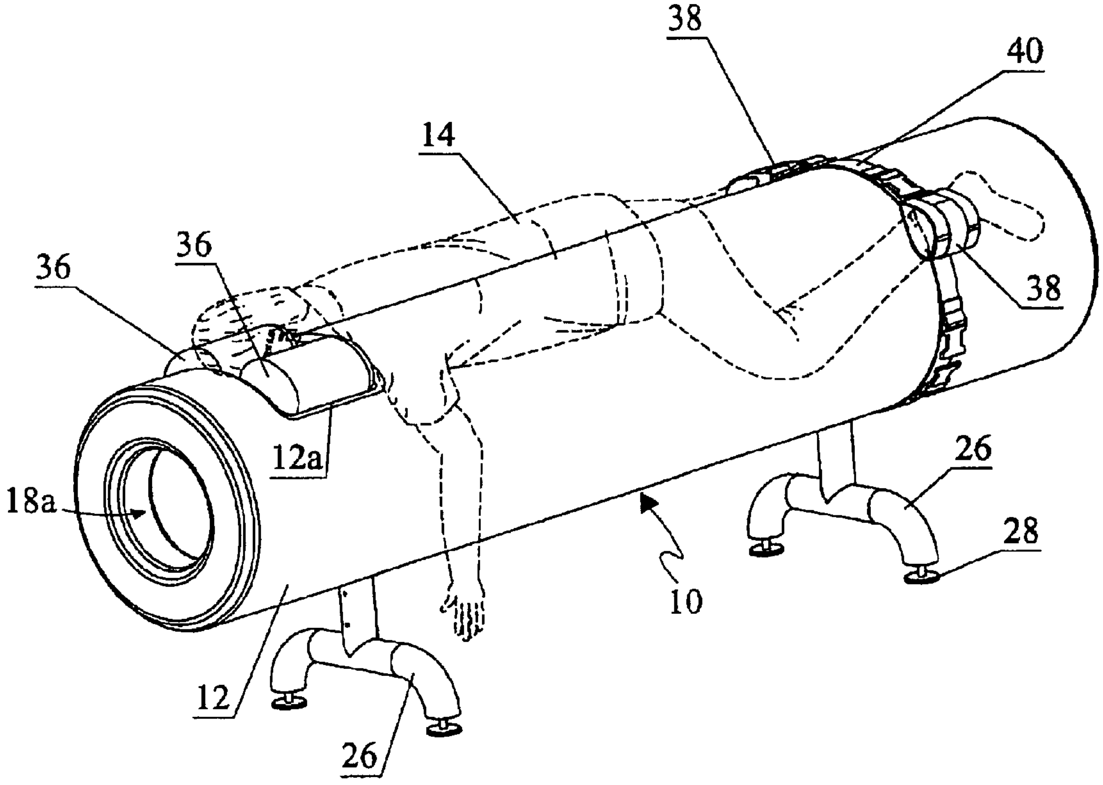
FIG. 2 is the table of FIG. 1 with a patient lying prone along and astride the upper surface and upper side of the table.
Figure 3:
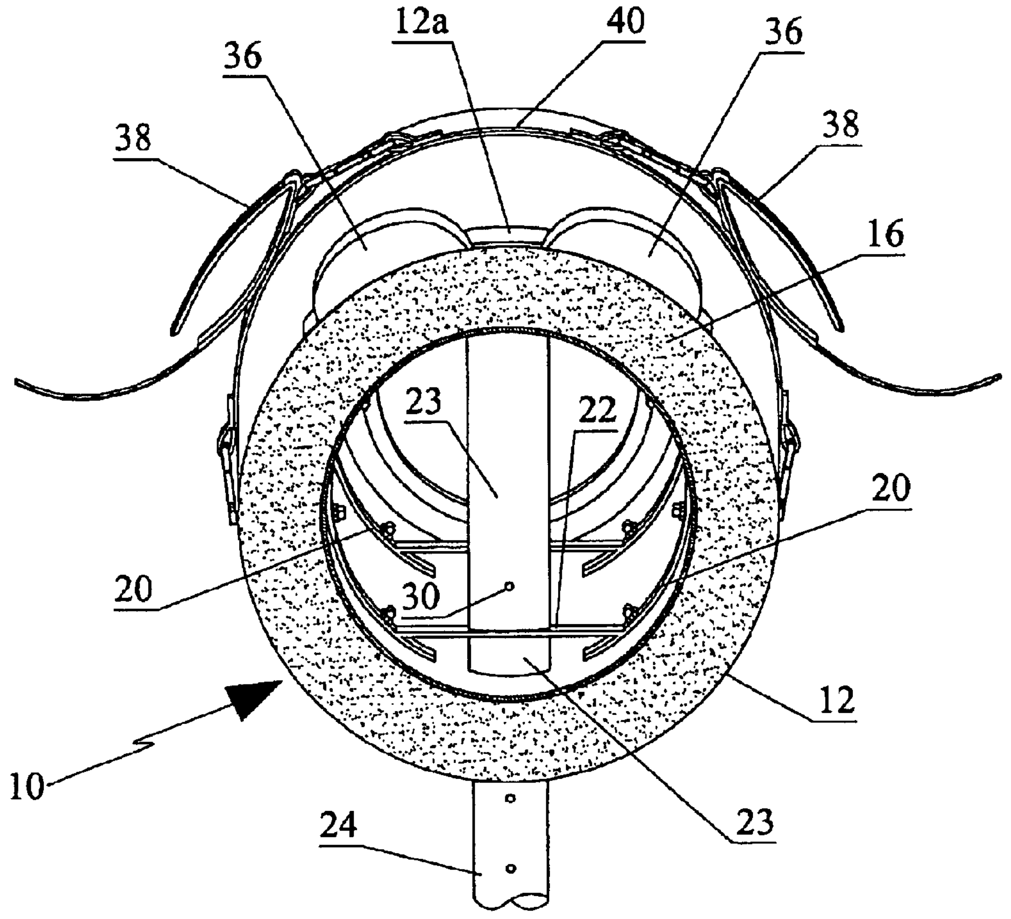
FIG. 3 is a rear end perspective of the table of FIG. 1.

As seen in FIG. 1, table 10 preferably has a generally cylindrical or tubular outer surface 12 on which a patient 14 such as seen in FIG. 2 may lie prone, aligned generally parallel to the longitudinal axis A of the table. Outer surface 12 is preferably resiliently padded for example by the use of a layer of resilient foam 16 wrapped around such as seen in FIG. 3, or otherwise formed on, or mounted to, at least the upper half of an internal core or frame (herein collectively referred to as a frame) as for example provided by rigid tube 18. Tube 18 may have an outside diameter of twelve inches and foam layer 16 may be three inches thick so as to add three inches to the radius of curvature of outer surface 12.

Figure 4:
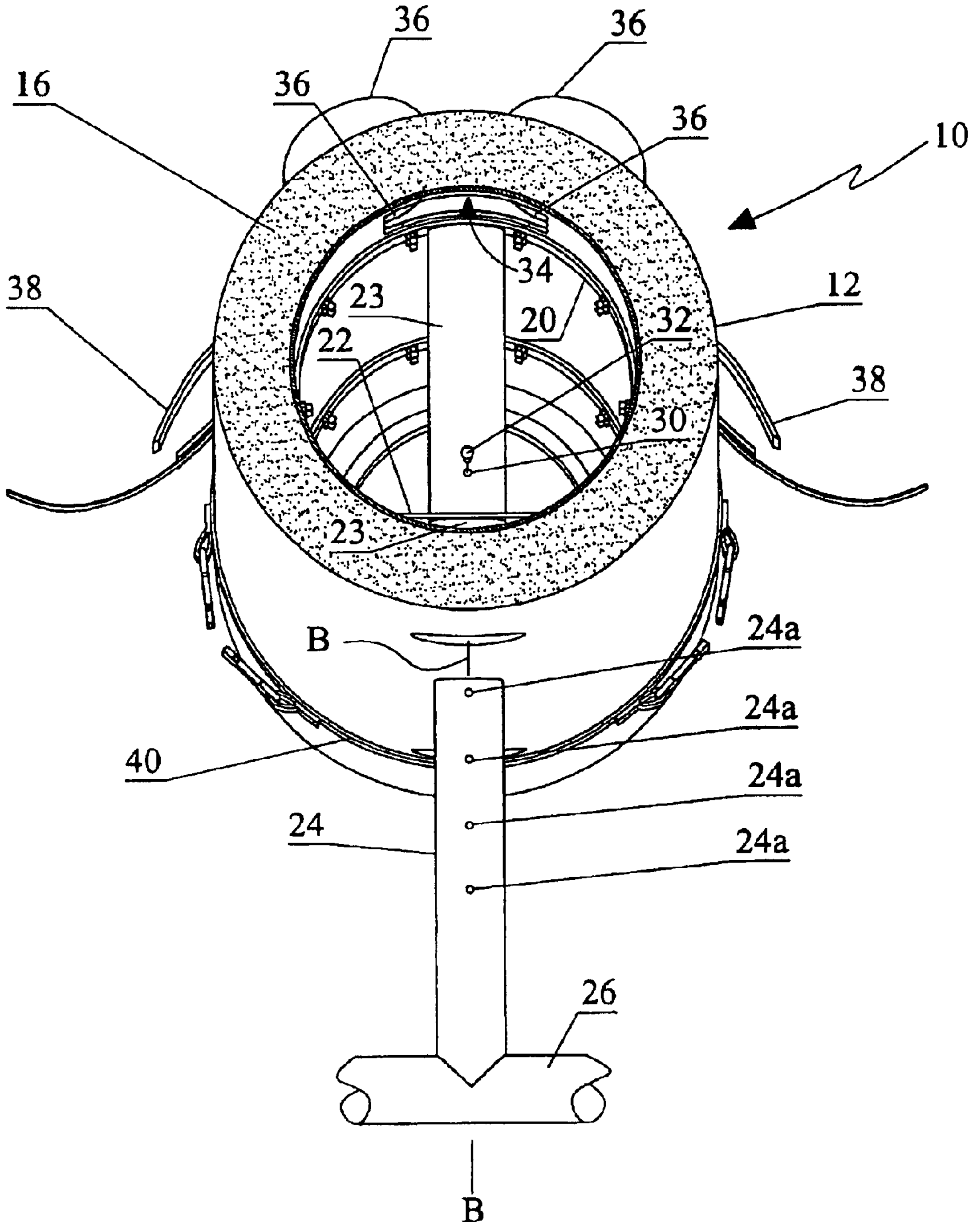
FIG. 4 is a front end perspective view of the table of FIG. 1.
Figure 5:
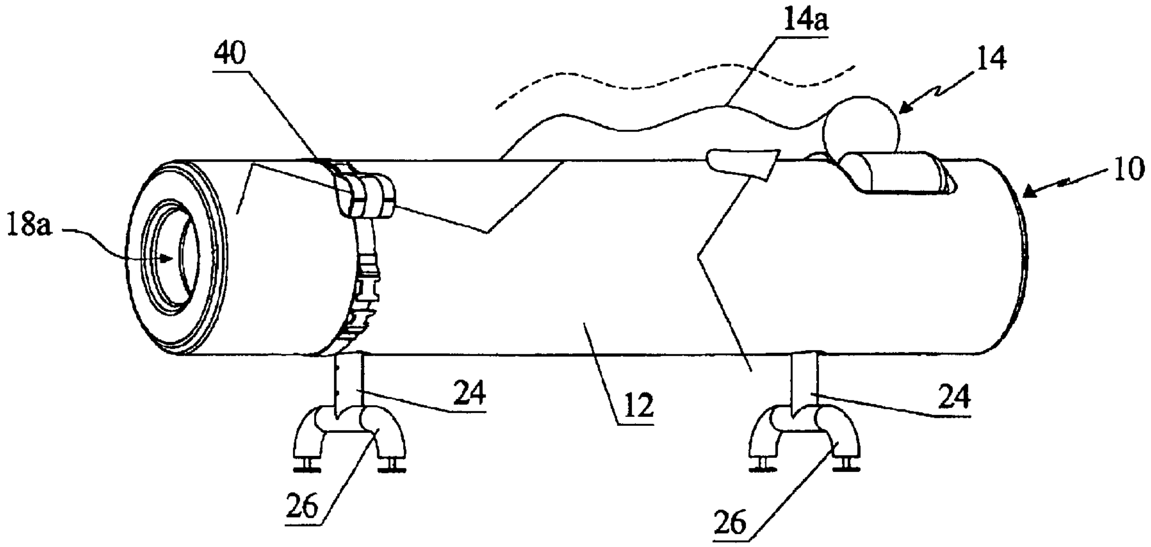
FIG. 5 is a diagrammatic view in side elevation of a patient lying prone on the table of FIG. 1.

In the embodiment illustrated, the radius of curvature of surface 12 such as seen in FIGS. 3 and 4 is a constant radius due to the cylindrical shape of tube 18 and the constant thickness of foam layer 16. However, this is not intended to be limiting as the circumference of outer surface 12 in lateral cross section orthogonal to axis A may define other than a circle. For example, the lateral cross section of outer surface 12 may be elliptical. By way of further example, outer surface 12 may be merely one half of a cylinder, or formed as a truncated cone so that, in lateral cross section, outer surface 12 is a semi-circle or parabolic. Outer surface 12 may also define a sector of a circle other than semicircular, or, in lateral cross section, may define an ogive, although preferably a dropped ogive so as to reduce the severity of the angularity of the vertex. Thus it will be understood that many such variations in the cross-sectional shape of the table surface are intended to be within the scope of the present invention so long as the table is elongate so that a patient may lie supine along it, or lie prone along it in a relaxed lordotic posture so that, as illustrated diagrammatically in FIG. 5, the spine 14*a* of patient 14 generally corresponds in shape to a lordotic curve (shown in dotted outline).

In the illustrated embodiment which, again, is not intended to be limiting, tube 18 has, at each end, a metal collar or sleeve 20 bolted into the tube. Sleeve 20 is sized to fit snugly into the ends of tube 18. Sleeve 20 is rigid, preferably of metal, so as to support a rigid base plate 22 mounted as by welding to sleeve 20 so as to extend horizontally across a lower portion of the sleeve. Plate 22, tube 18 and foam layer 16 have co-axially vertically aligned apertures therethrough. A hollow receiving tube or sleeve 23 is mounted through the apertures in plate 22 and tube 18 so that a rigid member such as post 24 may be snugly telescopically mounted along axis B into sleeve 23 through a lower opening in the end of the sleeve for vertical sliding telescopic movement of post 24 along axis B. Posts 24, one at each end of tube 18, and their corresponding cross-members and feet are one example, not intended to be limiting, of a base onto which may be mounted the frame of the present invention.

A supporting member or supporting structure such as cross arms 26 are rigidly mounted to posts 24, for example, one cross arm 26 for each post 24 as illustrated, so as to support the table on feet 28, where feet 28 may also be coasters or the like.

Because the pair of posts 24 are telescopically mounted in sleeve 23, the elevation of outer surface 12 and inclination of outer surface 12 relative to the floor surface may be adjusted. In the illustrated embodiment, not intended to be limiting, posts 24 each have an array of apertures or holes 24*a* formed vertically therealong. Apertures or holes 24*a* and a hole 30 on each of sleeves 23 are sized to receive a pin 32 journalled therethrough so that, once posts 24 have been telescoped to their desired position into, or out of, their corresponding sleeves 23, pin 32 may be inserted into one of holes 30 and a corresponding hole 24*a* in each post 24 so as to releasably lock the position of the posts relative to their corresponding sleeves so as to prevent further telescoping of posts 24 upwardly.

Outer surface 12 has a concavity 12*a* formed towards one end. An opening 34 may be formed in the corresponding upper surface of tube 18, centered within concavity 12*a*. A pair of resilient pillows 36, sized to snugly fit into concavity 12*a*, may be releasably mounted, for example by the use of hook and loop fasteners (not shown) into concavity 12*a*, preferably in parallel slightly spaced apart relation on either side of opening 34. Pillows 36 may in one embodiment be made of visco-elastic open-cell polyurethane foam such as made by Tempur™ of Sweden and Denmark. In the preferred embodiment, pillows 36 are sized so as to support the length of the face of patient 14 when the patient is prone on outer surface 12 with the patient's face resting on and symmetrically between pillows 36. Concavity 12*a* may cause pillows 36 to be slightly inwardly inclined toward each other into inclined opposed facing relation, or pillows 36 may otherwise be in planar relationship relative to each other so long as the face of patient 14 is comfortably supported and the relaxed lordotic posture is maintained or facilitated.

In keeping with having patient 14 in a relaxed lordotic posture when prone on outer surface 12, applicant has found it advantageous to support the legs of patient 14, for example by the use of ankle straps 38. Ankle straps 38 may be supported relative to outer surface 12 by encircling strap 40. Strap 40 supports a pair of ankle straps 38, one on either side of the ridge line of outer surface 12, for example by means of releasable clips 42. In use, ankle straps 38, which may be padded, may be wrapped around the ankles of patient 14 and releasably snugged onto the ankles by the use of hook and loop fasteners (not shown), and once so mounted to the ankles then clipped to encircling strap 40 by the use of clips 42. Encircling strap 40 is mounted onto outer surface 12 towards the end of table 10 opposite from concavity 12*a* so that patient 14 may comfortably lie draped in a "hugging" posture stably balanced on top of, and along, outer surface 12.

The opposite ends of foam layer 16, and the entire outer surface 12, may be enclosed as illustrated within a flexible covering, for example, of soft vinyl material. The exposed openings into cavity 18*a* of tube 18 which allow access to adjust the telescoping of posts 24, may be enclosed by removable covers (not shown) which may be releasably mounted for example again by the use of hook and loop fasteners.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A chiropractic table for treatment of a patient when the patient is in a lordotic, relaxed posture lying prone on the table, the table comprising:

a base, a padded frame mounted to said base, said padded frame to form an elongate upper surface extending in a generally horizontal longitudinal direction, said upper surface arcuately shaped, when viewed in lateral cross-section orthogonal to said longitudinal direction, so as to form downwardly curved sides extending downwardly and oppositely from an uppermost ridge-line surface extending the length of said upper surface, said ridge-line surface having a face-resting concavity formed thereon at a first end of said upper surface, said concavity adapted to receive in resting relation thereon the face of the patient when lying prone along and astride the ridge-line surface, a pair of patient leg supports mounted to a second end of said upper opposite said first end, said pair of patient leg supports for supporting the legs of the patient adjacent said curved sides when the patient is lying prone along and astride said ridge-line surface.

2. The apparatus of claim 1 wherein said concavity has an aperture therein, said aperture disposed in said ridge-line surface and between said downwardly curved sides, said aperture extending through said upper and through a corresponding portion of said padded frame.

3. The apparatus of claim 2 further comprising a pair of pillows mounted on either said of said aperture so that each side of the face of the patient rests on one of said pair of pillows when the patient is lying prone along and astride said ridge-line surface.

4. The apparatus of claim 3 wherein said pair of pillows are releasably mounted into said concavity and said concavity is formed so as to be recessed into said upper surface.

5. The apparatus of claim 1 wherein said base is a pair of upright supports, each upright support of said pair of upright supports mounted to said padded frame at each of said first and second ends respectively.

6. The apparatus of claim 5 wherein each said upright support comprises a post telescopically mounted to said padded frame for selectively vertically adjustable sliding of said post relative to said padded frame.

7. The apparatus of claim 6 wherein said padded frame is tubular so as to define a cavity along and within said padded frame, and wherein said padded frame is padded with resilient padding extending along said ridge-line surface and down said curved sides.

8. The apparatus of claim 7 wherein an outer surface of said padded frame is generally cylindrical, said outer surface including said upper surface.

9. The apparatus of claim 8 wherein said upright supports are mounted to said padded frame so as to extend telescopically into said cavity and wherein said pair of patient leg supports are a pair of ankle straps.

10. A chiropractic table for treatment of a patient when in a lordotic relaxed posture lying thereon, said table comprising:

a padded frame forming a generally tubular shape, said padded frame having first and second opposite ends, wherein said frame is covered, over at least an upper side thereof, with resilient padding, said upper side having a face-resting concavity formed thereon at said end, a pair of patient leg supports mounted to said second end, said pair of patient leg supports for supporting the legs of the patient when lying prone along and astride said upper side, wherein said concavity is adapted to receive in resting relation thereon the face of the patient, a base mounted to said padded frame.

11. The apparatus of claim 10 wherein said concavity has an aperture therein, said aperture lying along a ridge-line surface between downwardly curved sides of said padding.

12. The apparatus of claim 11 further comprising a pair of pillows mounted on either side of said aperture so that each side of the face of the patient on one of said pair of pillows when the patient is lying prone along and astride said ridge-line surface.

13. The apparatus of claim 12 wherein said pair of pillows are releasably mounted into said concavity and said concavity is formed so as to be recessed to said ridge-line surface.

14. The apparatus of claim 10 wherein said base is a pair of upright supports, each upright support of said pair of upright supports mounted to said padded frame at each of said first and second ends respectively.

15. The apparatus of claim 14 wherein each said upright support comprises a post telescopically mounted to said padded frame for selectively vertically adjustable sliding of said post relative to said padded frame.

16. The apparatus of claim 15 wherein an outer surface of said padding is generally cylindrical.

17. The apparatus of claim 10 wherein said pair of patient leg supports are a pair of ankle straps.

* * * * *